United States Patent
Hollidt et al.

(10) Patent No.: US 12,123,873 B2
(45) Date of Patent: Oct. 22, 2024

(54) LATERAL FLOW IMMUNOASSAY STRIP DEVICE

(71) Applicant: SANOFI, Paris (FR)

(72) Inventors: Jörg-M. Hollidt, Berlin (DE); Thomas Bogusch, Falkensee (DE); Franziska Werner, Berlin (DE); Hardy Kietzmann, Frankfurt am Main (DE)

(73) Assignee: SANOFI, Paris (FR)

( * ) Notice: Subject to any disclaimer, the term of this patent is extended or adjusted under 35 U.S.C. 154(b) by 725 days.

(21) Appl. No.: 17/043,742

(22) PCT Filed: Apr. 2, 2019

(86) PCT No.: PCT/EP2019/058224
§ 371 (c)(1),
(2) Date: Sep. 30, 2020

(87) PCT Pub. No.: WO2019/192978
PCT Pub. Date: Oct. 10, 2019

(65) Prior Publication Data
US 2021/0033605 A1    Feb. 4, 2021

(30) Foreign Application Priority Data
Apr. 3, 2018 (EP) .................... 18165380

(51) Int. Cl.
*G01N 33/543* (2006.01)
(52) U.S. Cl.
CPC . *G01N 33/54388* (2021.08); *G01N 33/54346* (2013.01); *G01N 33/54393* (2013.01); *G01N 2333/78* (2013.01); *G01N 2800/105* (2013.01)
(58) Field of Classification Search
None
See application file for complete search history.

(56) References Cited

U.S. PATENT DOCUMENTS

| | | | |
|---|---|---|---|
| 11,747,336 B1 * | 9/2023 | Ceballos | G01N 33/54346 435/5 |
| 2005/0196875 A1 * | 9/2005 | Blatt | G01N 33/558 436/514 |

(Continued)

FOREIGN PATENT DOCUMENTS

| | | |
|---|---|---|
| CN | 106370844 | 2/2017 |
| CN | 107688090 | 2/2018 |

(Continued)

OTHER PUBLICATIONS

Gong et al (Improved LFIAs for highly sensitive detection of BNP at point-of-care, Int J Nanomedicine. 2017; 12: 4455-4466.; IDS#7 (Year: 2017).*

(Continued)

*Primary Examiner* — Ann Montgomery
*Assistant Examiner* — Chau N. B. Tran
(74) *Attorney, Agent, or Firm* — SALIWANCHIK, LLOYD & EISENSCHENK (57) ABSTRACT

The invention relates to a lateral flow assay device for the detection of a target peptide in a liquid sample, comprising: (a) a solid support, (b) a sample pad for initially receiving and optionally pre-treating the sample at a first end of the solid support, (c) an absorbent pad at a second end of the solid support, (d) a conjugate pad comprising in a dry state a mobilizable conjugate of a particle and the target peptide, wherein the target peptide conjugated to said particle is biotinylated and the particle comprises on its surface a biotin-binding protein, (e) a target peptide reaction membrane comprising, (i) a capture region comprising an immobilized first capture reagent against the target peptide, and (ii) optionally a control region comprising an immobilized second capture reagent against particle control conjugate, wherein the sample pad, the conjugate pad, the reaction membrane and the absorbent pad are mounted to the solid (Continued)

support to permit capillary flow from the sample pad to the reaction membrane through the conjugate pad, and wherein the loading of the particle with the target peptide is from about 20% to about 55% of the maximal loading capacity of the particle.

8 Claims, 5 Drawing Sheets

(56) References Cited

U.S. PATENT DOCUMENTS

| | | | | |
|---|---|---|---|---|
| 2008/0138842 | A1* | 6/2008 | Boehringer | G01N 33/558 435/7.94 |
| 2018/0052153 | A1* | 2/2018 | Kidwell | G01N 11/02 |

FOREIGN PATENT DOCUMENTS

| | | |
|---|---|---|
| EP | 2 026 821 | 2/2009 |
| EP | 3 156 801 | 4/2017 |
| JP | H06-504846 | 6/1994 |
| JP | 2007-139538 | 6/2007 |
| JP | 2010-508513 | 3/2010 |
| JP | 2017-524671 | 8/2017 |
| WO | WO 92/12428 | 7/1992 |
| WO | WO 2008/057366 | 5/2008 |
| WO | WO 2015/195701 | 12/2015 |
| WO | WO-2023224993 A1 * | 11/2023 |

OTHER PUBLICATIONS

Hsieh et al. (Analytical Tools to Improve Optimization Procedures for Lateral Flow Assays, Diagnostics 2017, 7, 29) (Year: 2017).*

Qian et al. (Analysis of lateral flow biodetectors: competitive format, Analytical Biochemistry vol. 326(2): 211-224, 2004) (Year: 2004).*

Hu et al. (Enzyme immunosensor based on gold nanoparticles electroposition and Streptavidin-biotin system for detection of S. pullorum & S. gallinarum, Electrochimica Acta 117(2014) 239-245) (Year: 2014).*

Gong, Y et al. "Improved LFIAs for highly sensitive detection of BNP at point-of-care" *International Journal of Nanomedicine*, 2017, pp. 4455-4466, vol. 12.

Lee, K. M. et al. "Measurement of Urinary N-Telopeptides and Serum C-Telopeptides from Type I Collagen Using a Lateral Flow-Based Immunoassay" *Sensors*, Dec. 24, 2012, pp. 165-174, vol. 13, No. 1.

Rivas, L. et al. "Lateral Flow Biosensors Based on Gold Nanoparticles" *Gold Nanoparticles in Analytical Chemistry*, Chapter 14, 2014, pp. 459-605, vol. 66.

Written Opinion in International Application No. PCT/EP2019/058224, Apr. 18, 2019, pp. 1-7.

* cited by examiner

LATERAL FLOW IMMUNOASSAY STRIP DEVICE

CROSS-REFERENCE TO RELATED APPLICATION

This application is the U.S. national stage application of International Patent Application No. PCT/EP2019/058224, filed Apr. 2, 2019.

FIELD OF THE INVENTION

The present invention relates to the field of diagnostic methods and devices and in particular to lateral flow immunoassays.

BACKGROUND OF THE INVENTION

Lateral flow assays (LFA) are specific formats of diagnostic assays that are user-friendly, relatively cheap and fast. They can, for example, be used in point-of-care diagnostics and provide qualitative or quantitative detection of analytes such as polypeptides and nucleic acids in biological, environmental or food samples.

Lateral flow assays are composed of a chromatographic system in which the components of a sample such as blood or urine are transported through capillary forces to a reaction membrane. Immunochemical reactions (i.e. antibody-antigen) are often used for detection. The sample moves across the membrane via capillary force. Standard lateral flow assays have at least the following four parts: a sample pad, i.e. area on which the liquid sample is applied; a conjugate pad comprising labelled tags combined with capture reagents (e.g. antibodies); a reaction membrane (usually a nitrocellulose membrane) containing a test line and a control line for target antigen-antibody interaction; and an absorbent pad, which reserves the remaining sample (see Bahadir & Sezgintürk, Trends in Analytical Chemistry (2016) 82, 286-306; Sajid et al., J. Saudi Chem. Soc. (2015) 19, 689-705; Koczula & Gallotta, Essays in Biochemistry (2016) 60, 111-120, for review articles).

Typical set-ups of LFAs include sandwich immunoassays utilizing two different antibodies against the analyte to be detected and competitive immunoassays which comprises labelled analyte molecules competing with the unlabelled analyte molecules in the sample. Labels used for this purpose include nanoparticles such as gold or carbon nanoparticles and latex beads. Lateral flow assays are available for a number of different analytes including bacterial antigens (e.g. see WO 2014/059274 A1, WO 99/05524 A1) and protein biomarkers such as cardiac troponin I, myoglobin (e.g. see Zhu et al., Clinical Chemistry (2011) 57:12, 1732-1738) and collagen telopeptides (e.g. see Lee et al., Sensors (2013) 13, 165-174).

N- and C-terminal telopeptides of collagen (NTX and CTX, respectively) are markers for bone turnover (Lee et al., loc. cit.)). CTX-II, the human C-terminal cross-linked telopeptide of collagen type II, is for example known to be a marker for cartilage degradation e.g. in joint diseases such as osteoarthritis (OA) and rheumatoid arthritis (RA) (Christgau et al., Bone (2001) 29(3):209-15; Garnero et al., Ann. Rheum. Dis. (2001) 60:619-626; Mouritzen et al., Ann. Rheum. Dis. (2003) 62:332-336).

Immunoassays for the detection of CTX-II are commercially available, e.g. a competitive EIA and sandwich ELISA kits from LifeSpan Biosciences, Inc. (Seattle, Wash., USA). However, the available assays have a relatively low sensitivity and/or cannot be used at the point-of-care (POC).

SUMMARY OF THE INVENTION

The present invention provides lateral flow immunoassay methods and devices with a high sensitivity, a high dynamic range and which can be used at the POC, such as at the physician's office during the patient's visit. This contrasts with the methods available in the art, in which testing is confined to the medical laboratory, which entails sending off specimens away from the point of care and then waiting hours or days to learn the results, during which time care must continue without the desired information or is suspended until results are available.

In particular, the present invention pertains to a lateral flow assay device for the detection of a target peptide in a liquid sample, comprising:
 (a) a solid support,
 (b) a sample pad for initially receiving and optionally pre-treating the sample at a first end of the solid support,
 (c) an absorbent pad at a second end of the solid support,
 (d) a conjugate pad comprising in a dry state a mobilizable conjugate of a particle and the target peptide, wherein the target peptide conjugated to said particle is biotinylated and the particle comprises on its surface a biotin-binding protein,
 (e) a target peptide reaction membrane comprising,
  (i) a capture region comprising an immobilized first capture reagent against the target peptide, and
  (ii) optionally a control region comprising an immobilized second capture reagent against a control conjugate,
wherein the sample pad, the conjugate pad, the reaction membrane and the absorbent pad are mounted to the solid support to permit capillary flow from the sample pad to the reaction membrane through the conjugate pad.

Advantageously herein, the loading of the particle with the target peptide is from about 20% to about 55% of the maximal loading capacity of the particle.

The device is an immunochromatographic device for use in an immunoassay and is advantageously in a strip format. This device can in particular be used for the quantitative detection of a target peptide in a liquid sample.

The invention further relates to a method for the detection, particularly quantitative detection, of a target peptide in a liquid sample, comprising the steps of
 (a) applying said liquid sample to the sample pad of the device according to the invention, so as to permit flow of the sample from the sample pad through the conjugate pad to the reaction membrane,
 (b) detecting the presence or amount of the conjugate at the capture region, and
 (c) optionally detecting the presence or amount of the control conjugate at the control region,
wherein the presence or absence or the detected amount of the conjugate at the capture region is indicative for the absence or presence or the amount of the target peptide, respectively, in the liquid sample.

The device and method of the present invention are in particular aspects used for the detection of CTX-II. The device and method can be used in diagnostic and prognostic methods as well as in methods for stratifying subjects and/or during therapy monitoring. In case of the detection of CTX-II, the device and method of the invention can, for example, be used for diagnosing or prognosing patients with osteoarthritis.

DETAILED DESCRIPTION OF THE INVENTION

The present invention relates to a lateral flow assay device, particularly in strip format, for the detection of peptide analytes (oligopeptides, polypeptides, proteins) in liquid samples, especially in biological samples such as urine or blood. The assay is a competitive immunoassay that uses detectable particles that are conjugated to the target peptide. In the conjugate, the target peptide is biotinylated and the particle comprises a biotin-binding protein on its surface so that the biotin moiety of the target peptide is conjugated to the particles via the interaction of biotin with the biotin-binding protein. Suitable particles e.g. include gold nanoparticles and suitable biotin-binding proteins include neutravidin, streptavidin and avidin.

The present invention pertains to a lateral flow assay device for the detection of a target peptide in a liquid sample, comprising:
(a) a solid support,
(b) a sample pad for initially receiving and optionally pre-treating the sample at a first end of the solid support,
(c) an absorbent pad at a second end of the solid support,
(d) a conjugate pad comprising in a dry state a mobilizable conjugate of a particle and the target peptide, wherein the target peptide conjugated to said particle is biotinylated and the particle comprises on its surface a biotin-binding protein,
(e) a target peptide reaction membrane comprising,
(i) a capture region comprising an immobilized first capture reagent against the target peptide, and
(ii) optionally a control region comprising an immobilized second capture reagent against a control conjugate,
wherein the sample pad, the conjugate pad, the reaction membrane and the absorbent pad are mounted to the solid support to permit capillary flow from the sample pad to the reaction membrane through the conjugate pad.

In the device of the present invention, the loading of the particle with the target peptide is advantageously from about 20% to about 55% of the maximal loading capacity of the particle.

The device is a device for use in an immunoassay and is advantageously in a strip format. This device can in particular be used for the quantitative detection of a target peptide in a liquid sample. The test region and the control region (if present) are typically in the form of a line. Hence, they might herein also be referred to as "test line" and "control line", respectively.

The "control conjugate" may, for example, be a conjugate of a particle, such as a gold nanoparticle, with a control peptide that is then bound on the control region. The control peptide may advantageously be bound ("conjugated") non-covalently to the particle. The control region comprises a capture reagent, for example an antibody or antigen-binding fragment thereof against said control peptide or a binding protein able to bind the control peptide. Advantageously herein, the control peptide is a biotinylated control peptide and the control region comprises a biotin-binding protein such as neutravidin. An exemplary control peptide is bovine serum albumin (BSA), which is advantageously biotinylated. It is advantageous that the control peptide does not normally occur in the sample to be detected. The control conjugate—if present—is on the conjugate pad as the conjugate of the target peptide ("target conjugate" or "target peptide conjugate"). The target peptide conjugate and the control peptide conjugate can for example be mixed prior to addition to the conjugate pad of the device. A particular control conjugate therefore comprises a nanoparticle such as a colloid gold nanoparticle and a biotinylated control peptide such as BSA.

A "peptide" in the context of the present invention is a chain of amino acid monomers linked by peptide (amide) bonds. The term "peptides" herein comprises oligopeptides, polypeptides and proteins.

A "oligopeptide" in the context of the present invention is a single (typically) linear chain of typically 2 to 9 amino acid residues held together by amide bonds. A "polypeptide" in the context of the present invention is a single (typically) linear chain of many (typically 10 or more, and particularly 10 to about 100) amino acid residues, held together by amide bonds. Also proteins are peptides in the sense of the present invention. They are usually at least 50 amino acids in length and may comprise more than one polypeptide chain. While peptides in most cases are linear as indicated above, in some cases they may also be branched or cross-linked. Such peptides are also encompassed by the term "peptide" in the context of the invention.

Figure 1:
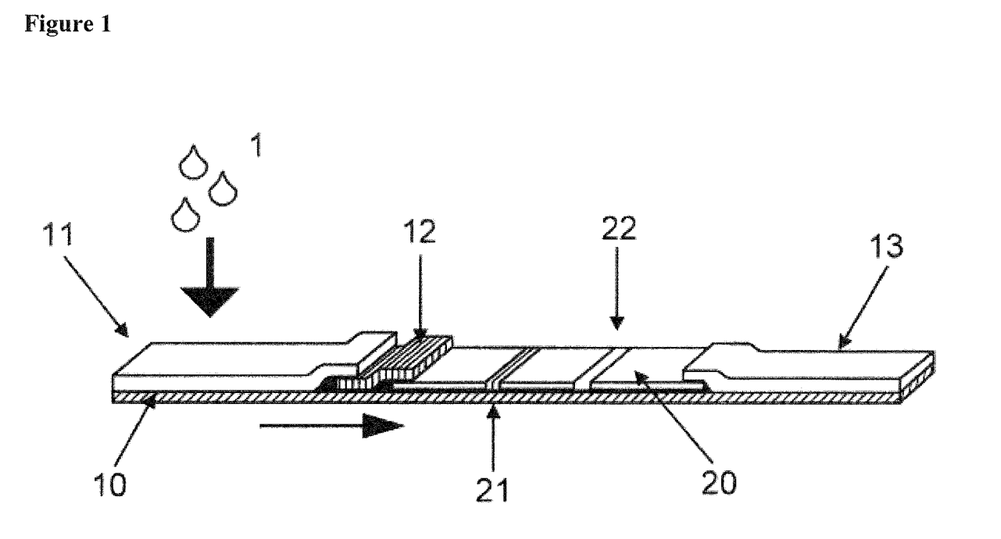
FIG. 1 shows an exemplary set-up for a lateral flow immunoassay of the invention. 1: sample; 10: solid support; 11: sample pad; 12: conjugate pad; 13: absorbent pad; 20: reaction membrane; 21: test line; 22: control line.

A typical set-up of the lateral flow assay device is shown in FIG. 1. The device has a solid support (10) on which the sample pad (11), the conjugate pad (12), the absorbent pad (13) and the reaction membrane (20) are mounted. The solid support ("backing card") provides support for the pads and membranes of the actual assay but are otherwise not involved in the reaction or flow of the sample and analyte. Backing cards are for example made of polyvinylchloride (PVC). The assembly of pads and membranes on the backing card will typically be in a plastic housing although this is not required. The housing typically has at least one opening ("sample port") over the sample pad for application of the sample. The control and test lines are visible (e.g. via an opening or window) to detect or measure the bound label. The housing prevents the user from applying the sample anywhere except the sample pad. The housing also serves to protect the strip from inadvertent splash onto the membrane. External labelling on the housing can also be used to indicate the position of test and control lines and provide other information. Housings can be obtained as off-the-shelf cassettes or custom-designed to fit around the strip.

Deciding between these options requires balancing unit cost, design costs, size compatibility with the strip, and requirements for external labelling. Internal pins and bars can be used to hold the strip in place relative to the sample port and viewing window. They hold the materials in intimate contact with one another while the test strip is running.

Materials used for the pads include porous matrices. Most commonly, cellulosic materials (i.e., filter papers) such as cotton linter are used for the pads. Glass fibre filters may also be used, however most commonly for the conjugate pad.

The "sample pad" receives the sample upon application and promotes the even distribution of the sample onto the conjugate pad. It may also influence the rate at which liquid enters the conjugate pad, preventing flooding of the device. In addition, the sample pad may also comprise additional components such as proteins, detergents, viscosity enhancers and buffer salts in order to process the sample (e.g. separation of sample components in the case of blood samples, removal of interferences, adjustment of pH, increasing the viscosity, solubilising components and/or preventing non-specific binding between conjugate and analyte or other components or to the reaction membrane).

The "conjugate pad" comprises the dried and mobilizable conjugate of the particle and the target peptide. When sample flows into the conjugate pad, the conjugate lifts off the pad material, and moves with the sample front into the reaction membrane. The sample pad thus delivers the conjugate (particle—target peptide) onto the reaction membrane in a consistent volume of sample on every test strip. If applicable, the conjugate pad will also comprise the dried and mobilizable control conjugate.

The device of the present invention has an "absorbent pad". The absorbent pad is placed at the distal end of the test strip and reserves the remaining sample. It wicks the fluid through the membrane and collects the processed liquid. Moreover, it increases the total volume of sample that enters the test strip.

The "reaction membrane" irreversibly binds capture reagents at the test and control lines. Typically, the reaction membrane is made from a polymer such as nitrocellulose, polyvinylidene fluoride, nylon or polyethersulfone. Nitrocellulose is by far the most suitable option for the reaction membrane. Nitrocellulose membranes bind proteins (such as antibodies or biotin-binding proteins) electrostatically through interaction of the strong dipole of the nitrate esters with strong dipoles of the peptide bonds within the protein.

The pads and in particular the reaction membrane may be protected by a cover tape. The cover tape must be transparent at least in the area of the test and control lines.

The "capture reagent" (also termed "biorecognition molecule" herein) herein refers to molecules that are able to specifically recognize the target peptide or in case of the control region the control peptide. Most commonly it is an antibody or an antigen-binding fragment thereof such as a Fab fragment. The antibodies may be monoclonal antibodies or polyclonal antibodies.

The "first capture reagent" is specific for the target peptide (independent of whether it is free in the sample (i.e. the unlabelled analyte) or conjugated to the particle (i.e. the "labelled" competing target peptide). The optional "second capture reagent" binds to the control conjugate (peptide, e.g. neutravidin as a capture molecule against a biotinylated control peptide such as BSA), i.e. it is a positive control.

The term "analyte" herein refers to the target molecule to be detected or measured in the sample. It is a peptide such as a protein or a shorter oligopeptide. The peptide at least has one epitope that can be specifically bound by the first capture reagent.

The "sample" may be a biological sample, an environmental sample or a food sample or the like. Biological samples such as bodily fluids like urine, whole blood, saliva, sweat, plasma or serum are the most common samples. Urine is the typical sample herein. In case of a blood sample, the device may comprise a filter matrix for separating blood cells from serum or plasma.

The sample can be diluted with a dilution buffer prior to addition to the sample pad. A typical dilution is 1:2 (sample: dilution buffer). Typical dilution buffers may for example comprise phosphate buffered saline (PBS), BSA and/or a non-ionic-surfactant such as Triton™ X-100.

The "particle" of the conjugate according to the invention serves as a detectable label (e.g. colored label) of the competing target peptide. In particular, the particle is selected from the group consisting of a colloid gold nanoparticle, a colored latex bead, a magnetic particle, a carbon nanoparticle, a selenium nanoparticle, a silver nanoparticle and a quantum dot. Colloid gold nanoparticles are particularly suitable in the context of the present invention. Such gold nanoparticles are commercially available, e.g. from Sigma-Aldrich, St. Louis, Mo., USA. Typically, the particle in the context of the present invention is essentially spherical and has a diameter of from 10 to 100 nm, advantageously 20 to 60 nm, most advantageously 40 nm. Gold nanoparticles of 40 nm diameter are most advantageous.

The "biotin-binding protein" in the context of the present invention may be selected from the group consisting of avidin, streptavidin and deglycosylated avidin. Deglycosylated avidin is known as neutravidin which is also the most suitable biotin-binding protein herein. These biotin-binding proteins are commercially available, e.g. from Thermo Fisher Scientific.

The target peptide and the control peptide to be conjugated to particles such as gold particles can be biotinylated using standard biotinylation reagents (e.g. a biotin n-hydroxysuccinimide ester (biotin-NHS)) which are commercially available (e.g. from Thermo Fisher Scientific).

During production of the target peptide conjugate, the particles such as gold nanoparticles are fully conjugated with the biotin-binding protein, i.e. the surface of the particle is saturated with the biotin-binding protein. Bovine serum albumin (BSA) can be added for blocking unspecific interactions. Hence, the particle may further comprise bovine serum albumin (BSA) on its surface. The biotin-binding proteins such as neutravidin are typically able to bind four biotin molecules. This ability can be used to conjugate biotinylated target peptide indirectly to the particles and adjust the loading (i.e. coating) of the particles with the target peptide. After the biotinylated target peptide is added to the complex of particle and biotin-binding protein, free biotin can optionally be added to the solution to saturate free biotin-binding sites of the biotin-binding protein.

The present inventors have found that a sub-maximal loading (coating) of the particles with the biotinylated target peptide lead to the best results in terms of sensitivity and dynamic range. Therefore, it is suitable herein that the loading (coating) of the particle with the target peptide is from about 20% to about 55% of the maximal loading (coating) capacity of the particle, typically from about 25% to about 50% of the maximal loading (coating) capacity of the particle, more typically from about 25% to about 45% of the maximal loading (coating) capacity of the particle, even more typically from about 25% to about 40% of the maximal loading (coating) capacity of the particle, more suitably about 25% to about 35% of the maximal loading (coating) capacity of the particle and most suitably about 30% of the maximal loading (coating) capacity of the particle. As typically the biotin-binding proteins such as neutravidin can bind a maximum of four biotin molecules, the loading of the particles with the target peptide in terms of absolute numbers can be calculated based on the above percentages. For example, a 1 ml solution of 40 nm gold nanoparticles OD 1 (at 526 nm) has a maximum binding capacity of about $4.17*10^{-11}$ mol neutravidin on its surface. This corresponds to about $1.67*10^{-10}$ mol biotin (or biotinylated target peptide) per ml 40 nm gold particle solution. A 30% loading with the biotinylated target peptide for example would thus correspond to about $5.2*10^{-11}$ mol biotinylated target peptide per ml 40 nm gold particle solution (OD 1 at 526 nm).

The reagents such as the target conjugates and optionally the control conjugates as well as the capture molecules can be dispensed to the pads or to the reaction membrane e.g. by using suitable dispenser platforms. For example the conjugates can be sprayed to the conjugate pad and the pads are then allowed to dry resulting in a dried but mobilizable conjugate on the conjugate pad.

The present invention also relates to a method for the detection of a target peptide in a liquid sample, comprising the steps of
 (a) applying said liquid sample to the sample pad of the device according to the invention, so as to permit flow of the sample from the sample pad through the conjugate pad to the reaction membrane,
 (b) detecting the presence or amount of the conjugate at the capture region, and
 (c) optionally detecting the presence or amount of the control conjugate at the control region,
wherein the presence or absence or the detected amount of the conjugate at the capture region is indicative for the absence or presence or the amount of the target peptide, respectively, in the liquid sample.

The method is particularly useful for the quantification of the target peptide in the sample.

Figure 2:
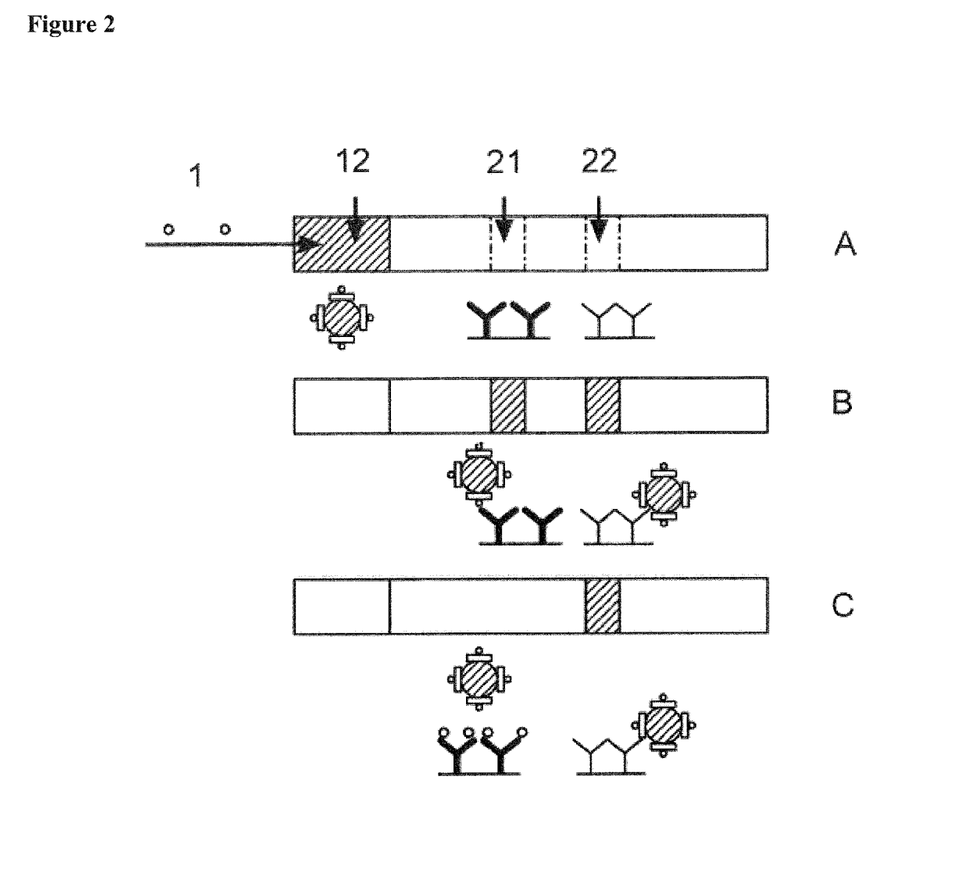
FIG. 2 shows an exemplary but typical set-up and course of the competitive LFA of the invention. A: prior to the start of the test; B: negative test; C: positive test. 1: Sample. 12: conjugate pad. 21: test line; 22: control line.

Hence, when performing the method of the present invention and/or when using the device of the invention for detecting or quantifying a target peptide, the sample (or the diluted sample as the case may be) is added to the sample pad (e.g. through the sample port in case a housing is used). The sample will then be transported through the conjugate pad to the reaction membrane. On the conjugate pad, the conjugates will be solubilised and transported to the reaction membrane. The intensity of the test line depends on the concentration of the analyte (i.e. the target peptide) in the original sample. The lower the concentration in the sample, the more intense the intensity will be due to the competition between the conjugated target peptide and the target peptide in the sample. The appended FIG. 2 illustrates the assay.

The intensity at the test line (and at the control line as the case may be) can be detected using an appropriate reader which is commercially available, e.g. from opTricon GmbH, Berlin, Germany. The device of the invention can be adapted for specific readers, e.g. by having a particular shape and dimension.

Further, the invention pertains to a kit for the detection of a target peptide in a liquid sample comprising a device of the invention. The kit may further comprise one or more containers comprising dilution buffer for diluting the sample prior to addition to the device and/or pipettes for adding the sample or diluted sample to the sample pad. The kit may also comprise instructions for use.

The device of the present invention or the kit of the present invention can be used for the quantification of a target peptide in a liquid sample. Depending on the nature of the target peptide, the device and kits can be used in the diagnosis or prognosis of a disease or condition. For instance, biomarkers (e.g. peptide hormones, marker proteins) that are indicative for a particular disease, condition or prognosis can be determined in the context of the present invention. In particular, the device, kit and method of the invention can be used for the diagnosis, prognosis, risk assessment, risk stratification, monitoring and/or therapy control of a subject. The term "subject" herein refers to a living human or non-human animal, such as a mammal, especially a human. The subject is most suitably a patient. The term "patient" as used herein refers to a living human or non-human animal (typically a human) that is receiving medical care or that should receive medical care due to a disease or medical condition. This includes persons with no defined illness who are being investigated for signs of pathology. Thus the methods and assays described herein are applicable to both, human and veterinary disease.

"Diagnosis" in the context of the present invention relates to the recognition and (early) detection of a disease or clinical condition in a subject and may also comprise differential diagnosis. Also the assessment of the severity of a disease or clinical condition may in certain embodiments be encompassed by the term "diagnosis".

"Prognosis" relates to the prediction of an outcome or a specific risk for a subject suffering from a particular disease or clinical condition. This may include an estimation of the chance of recovery or the chance of an adverse outcome for said subject.

"Monitoring" or "therapy monitoring" relates to keeping track of an already diagnosed disease, disorder, complication or risk, e.g. to analyze the progression of the disease or the influence of a particular treatment on the progression of disease or disorder. In the present invention, the term "risk stratification" relates to the grouping of subjects into different risk groups according to their further prognosis. Risk stratification also relates to stratification for applying preventive and/or therapeutic measures.

The term "patient management" in the context of the present invention refers to:
 the decision for admission to hospital or intensive care unit,
 the decision for relocation of the patient to a specialized hospital or a specialized hospital unit,
 the evaluation for an early discharge from the intensive care unit or hospital, and/or
 the allocation of resources (e.g. physician and/or nursing staff, diagnostics, therapeutics, surgery).

The term "assessment of disease severity" relates to the evaluation of the status of the disease in a patient including the progression of the disease, the likelihood of adverse events, the likelihood of high inpatient expenses and the likelihood of lengthy hospital stay or rehabilitation.

Hence, the present invention in one aspect relates to a method of diagnosing or prognosing a disease or condition, comprising the steps of
 (a) applying said liquid sample to the sample pad of the device according to the invention, so as to permit flow of the sample from the sample pad through the conjugate pad to the reaction membrane,
 (b) detecting the presence or amount of the conjugate at the capture region, and
 (c) optionally detecting the presence or amount of the control conjugate at the control region, wherein the presence or absence or the detected amount of the conjugate at the capture region is indicative for the absence or presence or the amount of the target peptide, respectively, in the liquid sample, and wherein the absence or presence or the amount of the target peptide in the liquid sample is indicative for the diagnosis or prognosis of said disease or condition.

Given the limitation of currently available investigations to measure the destruction of osteoarthritis (e.g. radiographic assessment of joint space narrowing is only an indirect index of cartilage loss), biological markers for cartilage degradation are much appreciated. For example, the target peptide can be C-terminal crosslinked telopeptide type II collagen (CTX-II) which is a marker for cartilage degradation and for the diagnosis of joint diseases such as osteoarthritis (OA) and rheumatoid arthritis (RA), particularly OA.

Type II Collagen is the predominant collagen in cartilage and is degraded by proteolytic enzymes secreted by the chondrocyte and synoviocytes. CTX-II peptides, released from the action of these enzymes, are eliminated in urine. Urine CTX-II is thus a biochemical sensitive marker of early cartilage degradation typically for subjects having osteoarthritis or rheumatoid arthritis (Garnero et al., 2000; loc. cit.).

Hence, the device may be used to detect cartilage degradation in a subject (typically a patient suffering from osteoarthritis, particularly of the knee or hip, more particularly knee osteoarthritis) and depending on the presence or degree of cartilage disease, a decision to treat the subject with a certain medication may be made.

A suitable medicament for the treatment of diseases associated with cartilage degradation, particularly osteoarthritis (e.g. of the knee or hip, typically osteoarthritis of the knee) and especially the treatment of pain associated with osteoarthritis are viscosupplements comprising hyaluronic acid (also called hyaluronan (HA)) or pharmaceutically acceptable salts or derivatives thereof such as sodium hyaluronate. The HA is often modified, e.g. by cross-linking. HA-based viscosupplements are typically administered intra-articularly, e.g. injected into the intra-articular space of a knee joint. A particular hyaluronan is "hylan G-F 20" which is comprised in products such as Synvisc® and Synvisc-One® (Sanofi). Such viscosupplements and corresponding dosage and administration schemes are, for example, described in U.S. Pat. No. 7,931,030 B1 and WO 2006/073835 A2.

HA may be of animal origin, e.g., derived from rooster combs or umbilical cords, or non-animal origin, e.g., bacterially fermented. Bacterially fermented HA can be produced as described in, e.g., Cooney et al. (1999) Biotechnol. Prog., 15:898-910. Bacterially fermented HA is also available commercially (e.g., Shiseido, Japan; Sigma-Aldrich, USA). As stated above, HA may be derivatized (e.g., crosslinked or otherwise modified or stabilized) or nonderivatized. Examples of crosslinkers include aldehyde, epoxide, polyaziril, glycidyl ether (e.g., 1,4-butanediol diglycidylether), and divinyl sulfone.

Hence, in the context of the present invention the terms "hyaluronic acid", "hyaluronan" and "HA" also encompass pharmaceutically acceptable salts or derivatives of hyaluronic acid and in particular "hylan G-F 20" and more in particular the products Synvisc® and Synvisc-One® (Sanofi).

The present invention, thus, also relates to a method of treating pain associated with a cartilage disease (i.e. alleviating the pain associated with a cartilage disease), particularly with osteoarthritis, more in particular with osteoarthritis of the hip or knee and especially with osteoarthritis of the knee, in a subject comprising determining the concentration of CTX-II in a urine sample of said subject using the device of the present invention, wherein depending on the concentration of CTX-II in the urine sample, the patient is treated with hyaluronic acid such as hylan G-F 20, e.g. Synvisc® or Synvisc-One®, or not or wherein the treatment regimen with hyaluronic acid such as hylan G-F 20, e.g. Synvisc® or Synvisc-One®, is determined based on the CTX-II concentration in said sample. Hyaluronic acid-containing medicaments such as hylan G-F 20, e.g. Synvisc® or Synvisc-One®, are typically injected into the affected joint, particularly the knee or hip. Similarly, the present invention relates to hyaluronic acid such as hylan G-F 20, e.g. Synvisc® or Synvisc-One®, for use in treating pain associated with cartilage disease, particularly with osteoarthritis, more in particular with osteoarthritis of the hip or knee and especially with osteoarthritis of the knee, in a subject, wherein the concentration of CTX-II is determined in a urine sample of said subject using the device of the present invention, and wherein depending on the concentration of CTX-II in the urine sample, the patient is treated with hyaluronic acid, such as hylan G-F 20, e.g. Synvisc® or Synvisc-One®, or not or wherein the treatment regimen with hyaluronic acid such as hylan G-F 20, e.g. Synvisc® or Synvisc-One®, is determined based on the CTX-II concentration in said sample.

Hence, in the context of the method of diagnosing or prognosing a disease or condition according to the present invention, said method may comprise the additional step of
  (d) prescribing to said subject a viscosupplement comprising hyaluronic acid or a pharmaceutically acceptable salt or derivative thereof such as hylan G-F 20, if the presence of CTX-II above a predetermined threshold is detected in the sample.

Also in the context of the method of diagnosing or prognosing a disease or condition according to the present invention, said method may comprise the additional step of
  (d) administering to said subject a viscosupplement comprising hyaluronic acid or a pharmaceutically acceptable salt or derivative thereof such as hylan G-F 20, if the presence of CTX-II above a predetermined threshold is detected in the sample.

Accordingly, the invention further relates to a viscosupplement comprising hyaluronic acid or a pharmaceutically acceptable salt or derivative thereof such as hylan G-F 20 for the use in the treatment of pain associated with a cartilage disease such as osteoarthritis in a subject, wherein the concentration of CTX-II is determined in a urine sample of said subject using the lateral flow assay device according to the invention, and wherein depending on the concentration of CTX-II in the urine sample, the viscosupplement is administered to said subject.

In other words, the invention further relates to a pharmaceutical composition comprising hyaluronic acid or a pharmaceutically acceptable salt or derivative thereof such as hylan G-F 20 for the use in the treatment of pain associated with a cartilage disease such as osteoarthritis in a subject, wherein the concentration of CTX-II is determined in a urine sample of said subject using the lateral flow assay device according to the invention, and wherein depending on the concentration of CTX-II in the urine sample, the pharmaceutical composition is administered to said subject.

Consequently, and as explained herein above, the present invention also relates to a method of treating pain associated with a cartilage disease such as osteoarthritis in a subject, comprising administering to said subject a viscosupplement comprising hyaluronic acid or a pharmaceutically acceptable salt or derivative thereof such as hylan G-F 20 (e.g. Synvisc® or Synvisc-One®), if the presence of CTX-II above a predetermined threshold is detected in a sample, particularly a urine sample, of said subject with a lateral flow assay device according to the present invention.

The present invention in one aspect relates to a lateral assay device for the detection of CTX-II in a urine sample, comprising:
(a) a solid support,
(b) a sample pad for initially receiving and optionally pre-treating the sample at a first end of the solid support,
(c) an absorbent pad at a second end of the solid support,
(d) a conjugate pad comprising in a dry state a mobilizable conjugate of a particle (particularly a gold nanoparticle) and CTX-II, wherein the CTX-II conjugated to said particle is biotinylated and the particle comprises on its surface a biotin-binding protein (particularly neutravidin),
(e) a reaction membrane comprising,
(i) a capture region comprising an immobilized first capture reagent (particularly an antibody) against the target peptide, and
(ii) optionally a control region comprising an immobilized second capture reagent (particularly neutravidin) against a control conjugate (particularly biotinylated BSA),
wherein the sample pad, the conjugate pad, the reaction membrane and the absorbent pad are mounted to the solid support to permit capillary flow from the sample pad to the reaction membrane through the conjugate pad.

It is suitable herein that the loading (coating) of the particle (particularly a gold nanoparticle) with the CTX-II is from about 20% to about 55% of the maximal loading (coating) capacity of the particle, typically from about 25% to about 50% of the maximal loading (coating) capacity of the particle, more typically from about 25% to about 45% of the maximal loading (coating) capacity of the particle, even more typically from about 25% to about 40% of the maximal loading (coating) capacity of the particle, more suitably about 25% to about 35% of the maximal loading (coating) capacity of the particle and most suitably about 30% of the maximal loading (coating) capacity of the particle.

Polyclonal antibodies against CTX-II can be produced by immunizing an animal such as a rabbit. The antibodies can then be purified e.g. from the serum of the animal e.g. by using affinity chromatography. Methods for the production of monoclonal or polyclonal antibodies are well known in the art.

When determining the concentration of a target peptide in a urine sample, the concentration of creatinine in said sample can be determined in addition, as a calibrator since urinary creatinine is (in the absence of renal diseases) relatively constant in an individual. For this purposes, the device may in addition comprise a reaction area ("creatinine reaction area") for a colorimetric or fluorimetric assay for the determination of creatinine. A part of the sample (or the diluted sample as the case may be) may be added to the creatinine assay to determine the creatinine concentration. In particular, this applies to the device and method for the detection of CTX-II according to the present invention.

The creatinine assay may for example be a lateral flow assay in strip format which is arranged in the device in parallel to the lateral flow immunoassay of the present invention. Hence, the creatinine assay may comprise a sample pad and a reaction area (similar to the reaction membrane of the lateral flow immunoassay).

The creatinine assay is typically a "dry chemistry" test, i.e. the assay comprises a mobilizable indicator dye (or a dye composition) in dry state, e.g. dried on an additional sample pad. A typical dye composition for the detection of creatinine comprises an oxidizable dye (such as quinoline), $Cu^{2+}$ ions and hydroxyperoxide. When creatinine is present in the sample, a complex between the cupric ions and creatinine will form. This $Cu^{2+}$-creatinine complex will oxidize the dye, particularly quinoline, in the presence of the hydroxyperoxide. The oxidation of the dye results in a change in color which can be detected using a reader. Suitable assays for the detection of creatinine are described for example in U.S. Pat. Nos. 5,374,561 and 6,001,656.

EXAMPLES

Example 1

Production of the CTX-II-Neutravidin-Gold Conjugate

All incubation steps (coupling, blocking, saturation etc.) are performed on a tumbler-shaker at room temperature.

Step 1—Neutravidin-Gold Conjugate:

7.5 µg neutravidin per 1 ml 40 nm colloidal gold $OD_{526\ nm}$ 1 solution were coupled in 5 mM sodium borate buffer for 2 h. Subsequently the solution was blocked with 1% BSA for 30 min. After centrifugation (including a wash step with 1% BSA), the conjugate pellet was resuspended in 2 mM borate buffer with 1% BSA and filtered at 0.22 µm. The result was a neutravidin-gold conjugate. It is assumed that the neutravidin-gold conjugate has a loading of 2.5 µg neutravidin per ml gold particles. Taking into account the molecular weight of neutravidin (60000 g/mol) this corresponds to a molar loading of $4.17*10^{-11}$ mol neutravidin per ml gold solution. Since one neutravidin molecule has four binding sites for biotin, theoretically $1.67*10^{-10}$ mol biotin molecules (and consequently the target peptide such as CTX-II) can bind to the neutravidin-gold conjugate per ml solution. This corresponds to a 100% loading herein.

7.5 µg gold are used for coupling to work in excess of gold and result in reproducible loading.

Step 2—CTX-II-Neutravidin-Gold Conjugate:

$5.2*10^{-11}$ mol biotinylated CTX-II per ml neutravidin-gold conjugate $OD_{526\ nm}$ 1 solution were coupled for 1 h in 2 mM borate buffer with 1% BSA. Subsequently, free biotin-binding sites were saturated for 1 h with $2.5*10^{-4}$ mol biotin per ml neutravidin-gold conjugate $OD_{526\ mn}$ 1. After centrifugation, the conjugate pellet was resuspended in resuspension buffer and filtered at 0.22 µm. The result was a CTX-II-neutravidin-gold conjugate.

1 ml neutravidin-conjugate $OD_{526\ nm}$ 1 can theoretically bind $1.67*10^{-10}$ mol biotin. The CTX-II antigen was synthetically biotinylated such that 1 mol CTX-II binds 1 mol biotin. Hence, in theory $1.67*10^{-10}$ mol biotinylated CTX-II bind to 1 ml neutravidin-gold conjugate, which corresponds to a 100% loading herein. By adding only $5.2*10^{-11}$ mol biotinylated CTX-II to 1 ml neutravidin-gold-conjugate, only about 30% oft he binding sites will be populated; hence, this is referred to as a 30% loading. In this case, the remaining 70% of the binding sites will be saturated with biotin added in excess.

Example 2

CTX-II Immunoassay

Principle of the Assay

The CTX-II Lateral Flow Device (LFD) is a competitive immunoassay (see FIGS. 1 and 2) with the following components:
Sample: human urine with CTX-II as analyte (diluted 1:2 with PBS comprising Triton™ X-100;
Conjugate pad: conjugate of colloid gold nanoparticle and CTX-II and control conjugate of colloid gold nanoparticle and biotinylated BSA;
Test line: anti-CTX-II antibody.

The CTX-II in the sample and the gold-CTX-II conjugate compete for binding to the test line (anti-CTX-H antibodies). When the gold-conjugate binds to the test line, the test line appears red (in case of relatively low CTX-II concentrations in the sample). The gold particles serve as the colored label. The more CTX-II is in the sample, the lower is the intensity of the test line. The color intensity of the test line is read out using a reader and is converted into a concentration using a pre-recorded calibration curve. The control line (positive control) serves for validating the test.

Figure 3:
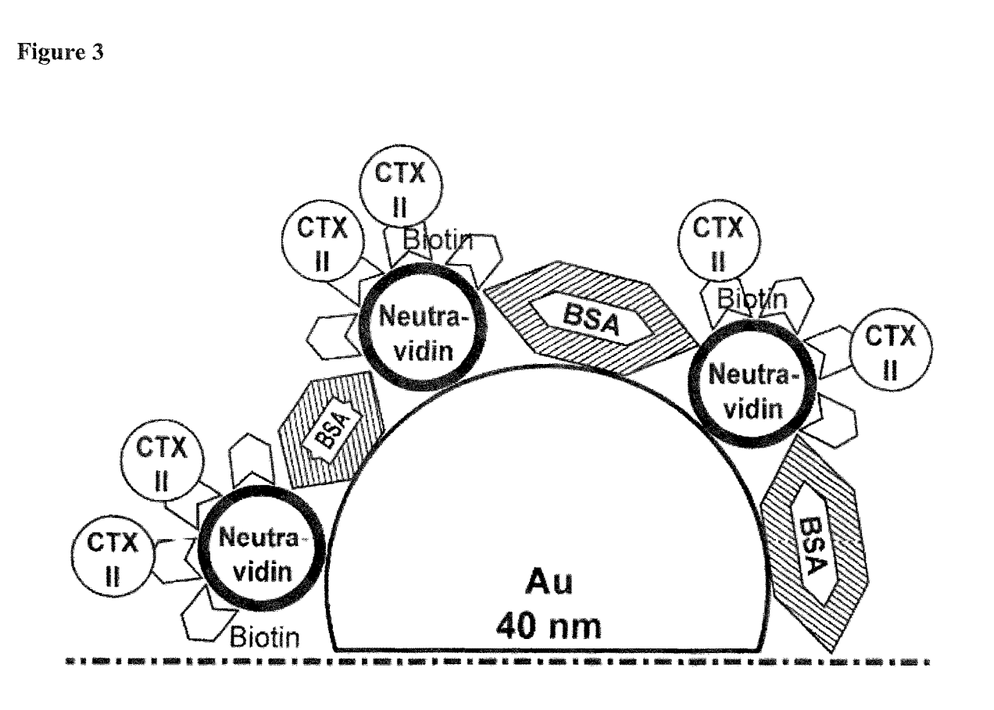
FIG. 3 shows a conjugate of the present invention which is 50% loaded with CTX-II.

The gold nanoparticles are fully conjugated with neutravidin (and BSA for blocking unspecific interactions) in order to assure reproducibility and stability. Neutravidin is able to bind four biotin molecules. This ability is used to conjugate biotinylated CTX-II indirectly to the gold nanoparticles and adjust CTX-II loading of the gold nanoparticles (see FIG. 3).

Materials and Methods

The gold-CTX-II conjugate was assembled as follows: 40 nm gold particles were conjugated with neutravidin (5 µg neutravidin per ml OD 1 gold nanoparticle suspension (Sigma-Aldrich or BBI Solutions)), then blocked with bovine serum albumin (BSA). (OD: optical density (OD 1=optical density of 1)). The conjugated neutravidin was then loaded with biotinylated CTX-II. After incubation with CTX-II, free biotin was added to the solution to saturate free biotin-binding sites of neutravidin.

To calculate the amount of CTX-II for loading, it was assumed that 2.5 µg neutravidin actually bind per ml gold particle suspension and 1 mol neutravidin binds to 4 mol biotin.

Figure 4:
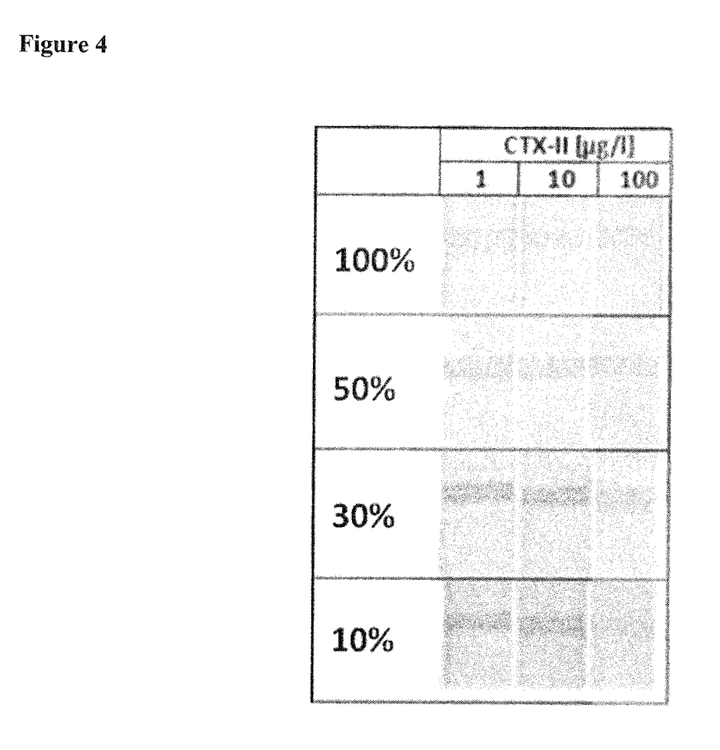
FIG. 4 illustrates the intensities of the test line at different loadings (10%, 30%, 50%, 100%) with CTX-II on the particle and different concentrations of CTX-II in the sample.

Results (Also See FIGS. 4 and 5):
a) At 100% loading (CTX-II in excess for conjugation):
low intensity of the test line at a CTX-II concentration in the sample of 0 µg/l.
no visually recognizable reduction of the intensity of the test line at a CTX-II concentration in the sample of 10 µg/l (the competition was visually detectable only at 100 µg/l CTX-II).
Hence, CTX-II loading should be decreased for sensitivity.
b) At 50% loading:
sensitivity like 100% loading but test line at 0 µg/l CTX-II more intense.
c) At 30% loading:
strong intensity of the test line at 0 µg/l CTX-II.
visually recognizable reduction of the test line intensity at 10 µg/l CTX-II.
d) At 10% loading:
strong intensity of the test line; no visually detectable reduction in intensity due to CTX-II in the sample.

CONCLUSION

Figure 5:
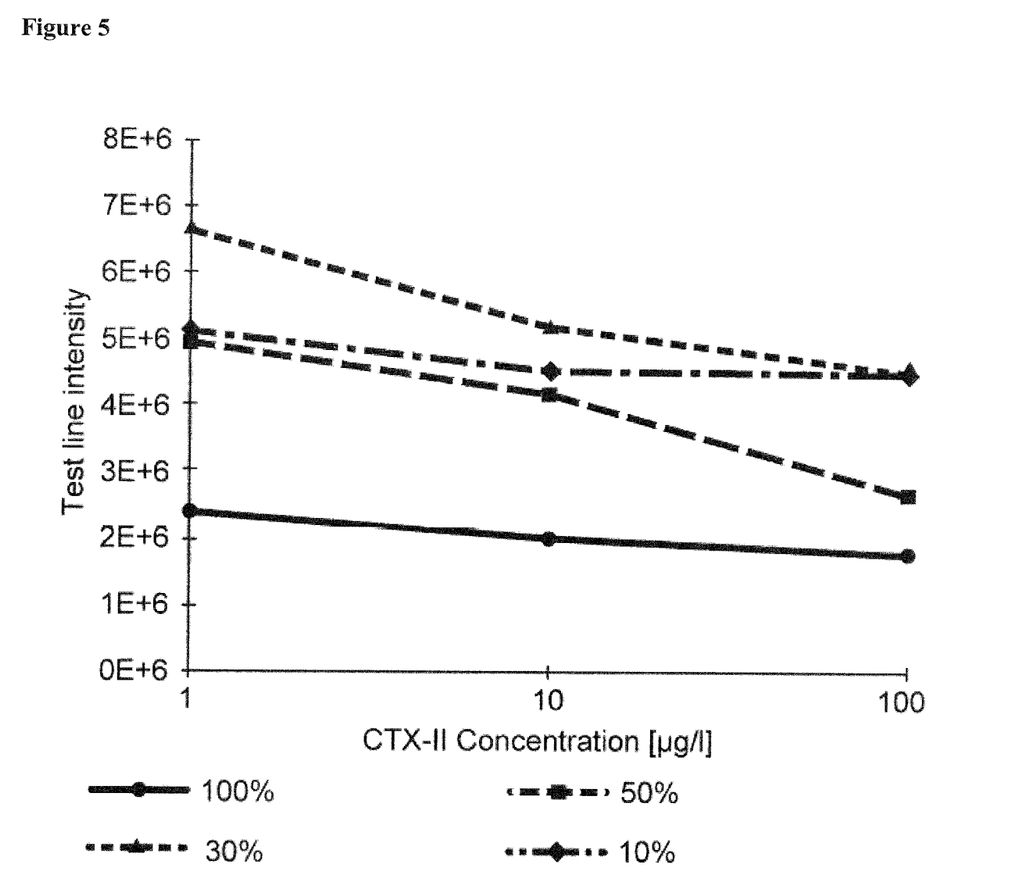
FIG. 5 shows the intensity (as read out by the reader) in units for different CTX-II concentrations in the sample and at different CTX-II loadings of the conjugate (logarithmic scale).

Indirect coupling (e.g. via neutravidin) allows in general for the adjustment of the loading of the particle with CTX-II to optimize the assay and, in particular, to reduce the loading to the optimal 30% loading in the present case. At this loading, the staining of the test line is pronounced at low CTX-II concentrations in the sample and low at high CTX-II concentrations. The visual inspection (FIG. 4) was verified using a reader (FIG. 5). Such an optimization allows for a high sensitivity over a broad concentration range which is not possible using prior art methods.

A 100% loading requires the reduction of the overall conjugate concentration in the assay such that the intensity of the test line was very weak even at low CTX-II concentrations and the signal strength was outside the linear range of the reader.

An inverse set-up (i.e. a non-competitive assay; anti-CTX-II antibodies conjugated of the gold nanoparticles, CTX-II at the test line) was also tested. However, it resulted in an insufficient sensitivity, since a 100% loading was required. Moreover, this inverse set-up is more expensive than the competitive set-up.

The documents cited herein are incorporated by reference in their entirety.

The invention claimed is:

1. A lateral flow assay device for the detection of a target peptide in a liquid sample, comprising:
(a) a solid support,
(b) a sample pad for initially receiving and optionally pre-treating the liquid sample at a first end of the solid support,
(c) an absorbent pad at a second end of the solid support,
(d) a conjugate pad comprising in a dry state a mobilizable conjugate of a particle and the target peptide, wherein the target peptide conjugated to said particle is biotinylated and the surface of the particle is fully saturated with a biotin-binding protein,
(e) a target peptide reaction membrane comprising,
  (i) a capture region comprising an immobilized first capture reagent against the target peptide, and
  (ii) optionally a control region comprising an immobilized second capture reagent against particle control conjugate,
wherein the sample pad, the conjugate pad, the reaction membrane and the absorbent pad are mounted to the solid support to permit capillary flow from the sample pad to the reaction membrane through the conjugate pad,
wherein loading of the particle with the target peptide is from about 20% to about 55% of the maximal loading capacity of the particle,
wherein said particle further comprises bovine serum albumin (BSA) on its surface for blocking unspecific interactions, and
wherein the particle is a colloid gold nanoparticle.

2. The lateral flow assay device of claim 1, wherein the device is a strip device or an immunochromatographic strip device.

3. The lateral flow assay device of claim 1, wherein the particle is essentially spherical and has a diameter of from 10 to 100 nm.

4. The lateral flow assay device of claim 1, wherein the biotin-binding protein is selected from the group consisting of avidin, streptavidin and deglycosylated avidin.

5. The lateral flow assay device of claim 4, wherein the deglycosylated avidin is neutravidin.

6. The lateral flow assay device of claim 1, wherein the loading of the particle with the target peptide is from about 20% to about 35% of the maximal loading capacity of the particle.

7. The lateral flow assay device of claim 1, wherein the liquid sample is a bodily fluid selected from the group consisting of urine, plasma serum, whole blood, sweat and saliva, typically urine.

8. The lateral flow assay device of claim 1, wherein the target peptide is C-terminal crosslinked telopeptide type II collagen (CTX-II).

* * * * *

UNITED STATES PATENT AND TRADEMARK OFFICE
CERTIFICATE OF CORRECTION

PATENT NO. : 12,123,873 B2
APPLICATION NO. : 17/043742
DATED : October 22, 2024
INVENTOR(S) : Jörg-M. Hollidt et al.

It is certified that error appears in the above-identified patent and that said Letters Patent is hereby corrected as shown below:

In the Specification

Column 12,
Line 52, "$OD_{526\ mn}$" should read --$OD_{526\ nm}$--.

Signed and Sealed this
Twenty-third Day of December, 2025

John A. Squires
*Director of the United States Patent and Trademark Office*